(12) United States Patent
Iga et al.

(10) Patent No.: US 10,438,047 B2
(45) Date of Patent: Oct. 8, 2019

(54) CELL ANALYSIS DEVICE AND CELL ANALYSIS METHOD

(71) Applicant: OLYMPUS CORPORATION, Tokyo (JP)

(72) Inventors: Yasunobu Iga, Tokyo (JP); Shinichi Takimoto, Tokyo (JP); Yohei Tanikawa, Tokyo (JP); Yoshinobu Akahori, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 86 days.

(21) Appl. No.: 15/725,413

(22) Filed: Oct. 5, 2017

(65) Prior Publication Data

US 2018/0032787 A1 Feb. 1, 2018

Related U.S. Application Data

(63) Continuation of application No. PCT/JP2015/060836, filed on Apr. 7, 2015.

(51) Int. Cl.
*G06K 9/00* (2006.01)
*C12M 1/00* (2006.01)
(Continued)

(52) U.S. Cl.
CPC ............ *G06K 9/0014* (2013.01); *C12M 1/00* (2013.01); *C12M 41/36* (2013.01); *C12Q 1/06* (2013.01); *G06K 9/00134* (2013.01); *G06T 7/0002* (2013.01); *G06T 7/13* (2017.01); *G01N 2015/0693* (2013.01); *G01N 2015/1486* (2013.01); *G06T 2207/30024* (2013.01); *G06T 2207/30168* (2013.01); *G06T 2207/30242* (2013.01)

(58) Field of Classification Search
None
See application file for complete search history.

(56) References Cited

U.S. PATENT DOCUMENTS

2007/0063142 A1   3/2007 Kanegasaki et al.

FOREIGN PATENT DOCUMENTS

JP         10031165 A   *  2/1998
JP      H10-031165 A      2/1998
(Continued)

OTHER PUBLICATIONS

International Search Report dated Jul. 7, 2015 issued in PCT/JP2015/060836.

*Primary Examiner* — Delomia L Gilliard
(74) *Attorney, Agent, or Firm* — Scully, Scott, Murphy & Presser, P.C.

(57) ABSTRACT

For the purpose of counting the number of cells within a culture container readily and accurately, a cell analysis device includes a cell-image acquiring unit that acquires an image of cells within a culture container in which the cells are cultured, a usability determining unit that determines whether or not the image acquired by the cell-image acquiring unit is usable, a number-of-cells counting unit that counts the number of cells within the image determined as being usable by the usability determining unit, and a number-of-cells calculating unit that calculates the number of cells within the culture container based on the number of cells counted by the number-of-cells counting unit.

8 Claims, 5 Drawing Sheets

(51) Int. Cl.
*C12Q 1/06* (2006.01)
*G06T 7/13* (2017.01)
*G06T 7/00* (2017.01)
*C12M 1/34* (2006.01)
*G01N 15/06* (2006.01)
*G01N 15/14* (2006.01)

(56) References Cited

FOREIGN PATENT DOCUMENTS

| | | | | |
|---|---|---|---|---|
| JP | 2004-016194 A | | 1/2004 | |
| JP | 2004016194 A | * | 1/2004 | ............ C12M 23/50 |
| JP | 2005-502369 A | | 1/2005 | |
| JP | 2005-107302 A | | 4/2005 | |
| JP | 2006-171574 A | | 6/2006 | |
| JP | 2007-078614 A | | 3/2007 | |
| JP | 2007-124913 A | | 5/2007 | |
| JP | 2009-194584 A | | 8/2009 | |
| JP | 2015-091220 A | | 5/2015 | |
| WO | WO 03/023571 A2 | | 3/2003 | |
| WO | WO 2007/103406 A2 | | 9/2007 | |
| WO | WO-2007103406 A2 | * | 9/2007 | ........... C12Q 1/6827 |

* cited by examiner

CELL ANALYSIS DEVICE AND CELL ANALYSIS METHOD

CROSS-REFERENCE TO RELATED APPLICATIONS

This is a continuation of International Application PCT/JP2015/060836, with an international filing date of Apr. 7, 2015, which is hereby incorporated by reference herein in its entirety. This application claims the benefit of International Application PCT/JP2015/060836.

TECHNICAL FIELD

The present invention relates to cell analysis devices and cell analysis methods.

BACKGROUND ART

A known method of counting the number of cells within a culture container involves counting the number of cells by recognizing the shapes of cells from a phase-contrast image (for example, see Patent Literature 1).

CITATION LIST

Patent Literature

{PTL 1}
Japanese Unexamined Patent Application, Publication No. 2007-78614

SUMMARY OF INVENTION

Technical Problem

An object of the present invention is to provide a cell analysis device and a cell analysis method with which the number of cells within a culture container can be counted readily and accurately.

Solution to Problem

An aspect of the present invention provides a cell analysis device including a cell-image acquiring unit that acquires an image of cells within a culture container in which the cells are cultured, a usability determining unit that determines whether or not the image acquired by the cell-image acquiring unit is usable, a number-of-cells counting unit that counts the number of cells within the image determined as being usable by the usability determining unit, and a number-of-cells calculating unit that calculates the number of cells within the culture container based on the number of cells counted by the number-of-cells counting unit.

In the above aspect, the usability determining unit may detect blurriness in the image and may determine that the image is usable if the image has no blurriness.

In the above aspect, the usability determining unit may detect whether or not an edge of the culture container appears in the image and may determine that the image is usable if the edge of the culture container does not appear in the image.

In the above aspect, the usability determining unit may detect whether or not an exterior of the culture container appears in the image and may determine that the image is usable if the exterior of the culture container does not appear in the image.

In the above aspect, the number-of-cells calculating unit may calculate the number of cells by using an average value of the number of cells counted from a plurality of images, and the usability determining unit may detect whether or not the image is identical to an already-acquired image and may determine that the image is usable if the image is not identical to the already-acquired image.

Another aspect of the present invention provides a cell analysis method including a photographing step of acquiring an image of cells within a culture container in which the cells are cultured, a usability determining step of determining whether or not the image acquired in the photographing step is usable, a number-of-cells counting step of counting the number of cells within the image determined as being usable in the usability determining step, and a number-of-cells calculating step of calculating the number of cells within the culture container based on the number of cells counted in the number-of-cells counting step.

In the above aspect, the usability determining step may include detecting blurriness in the image and determining that the image is usable if the image has no blurriness.

In the above aspect, the usability determining step may include detecting whether or not an edge of the culture container appears in the image and determining that the image is usable if the edge of the culture container does not appear in the image.

In the above aspect, the usability determining step may include detecting whether or not an exterior of the culture container appears in the image and determining that the image is usable if the exterior of the culture container does not appear in the image.

In the above aspect, the number-of-cells calculating step may include calculating the number of cells by using an average value of the number of cells counted from a plurality of images, and the usability determining step may include detecting whether or not the image is identical to an already-acquired image and determining that the image is usable if the image is not identical to the already-acquired image.

DESCRIPTION OF EMBODIMENTS

A cell analysis device 1 according to an embodiment of the present invention will be described below with reference to the drawings.

Figure 1:
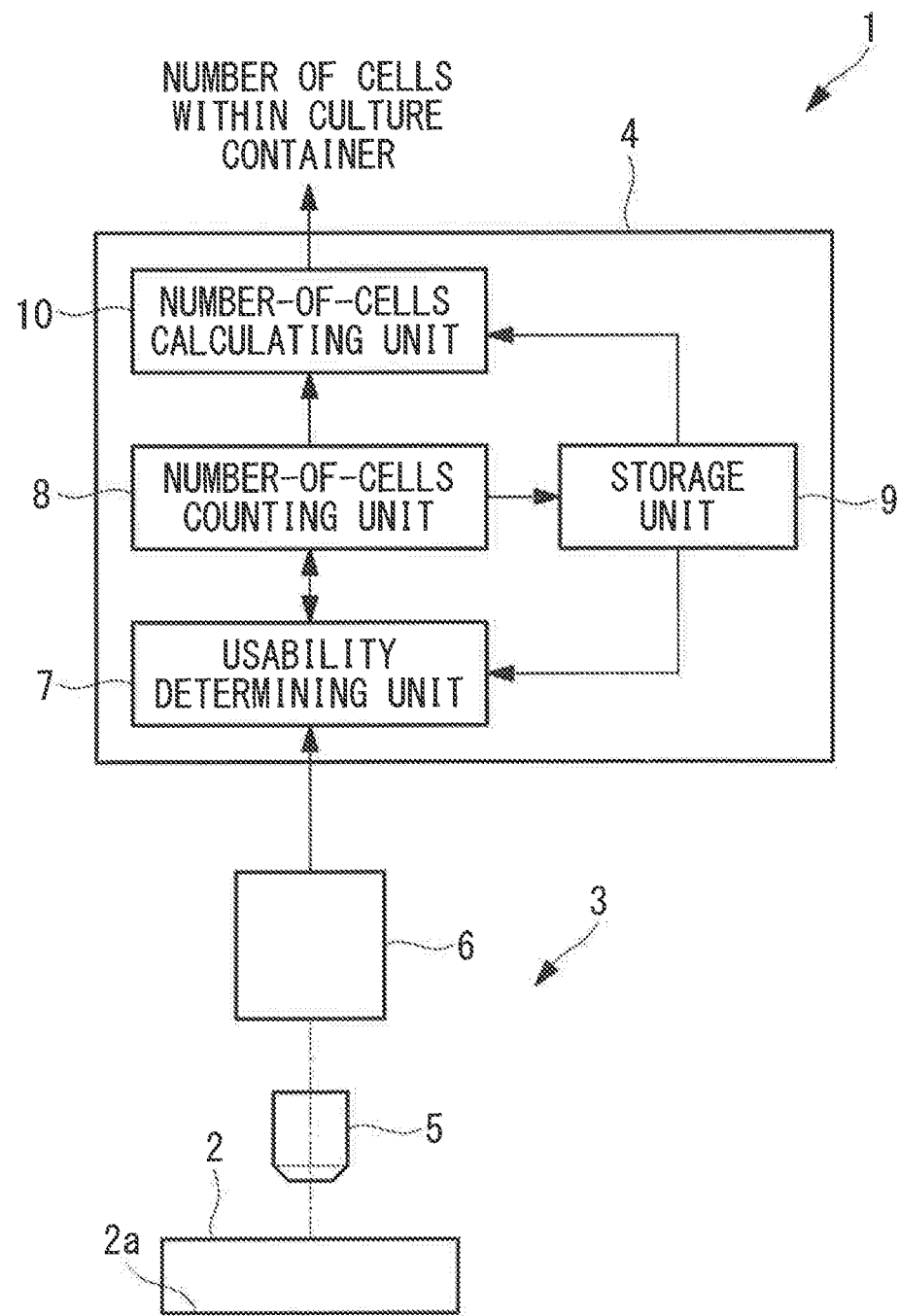
FIG. 1 illustrates the overall configuration of a cell analysis device according to an embodiment of the present invention.

As shown in FIG. 1, the cell analysis device 1 according to this embodiment includes a cell-image acquiring unit 3 that acquires an image of cells cultured within a culture container 2, and also includes an image processing unit 4 that processes the image acquired by the cell-image acquiring unit 3 and outputs the number of cells within the culture container 2.

The cell-image acquiring unit 3 includes an objective lens 5 that is disposed facing a culture surface 2a of the culture container 2 in which cells are cultured and that collects light from the culture surface 2a, and also includes a light detector 6 that photographs the light collected by the objective lens 5 so as to acquire an image of a predetermined field-of-view range within the culture surface 2a.

The acquired image is, for example, a phase-contrast image.

The image processing unit 4 includes a usability determining unit 7 that determines whether or not the cell image acquired by the light detector 6 is usable, a number-of-cells counting unit 8 that counts the number of cells within the image determined that it is usable by the usability determining unit 7, a storage unit 9 that stores the counted number of cells, and a number-of-cells calculating unit 10 that calculates the number of cells within the culture container 2 based on the number of cells counted by the number-of-cells counting unit 8.

The usability determining unit 7 performs the determination on the acquired image with respect to at least one of the following criteria:

(1) whether there is blurriness in the image;
(2) whether an edge of the culture container 2 appears in the image;
(3) whether the exterior of the culture container 2 appears in the image; and
(4) whether the image is identical to an already-acquired image.

If there is blurriness in the image, a linear pattern would form so as to extend substantially in the same direction as the direction in which the blurriness has occurred. Therefore, by determining whether or not there is a linear pattern extending substantially in the same direction, it can be determined whether or not there is blurriness. It is readily possible to detect whether or not there is a linear pattern by performing Fourier transformation on an image signal. The usability determining unit 7 determines that the image is usable when there is no blurriness in the image.

If an edge of the culture container 2 appears in the image, the image would have a pattern that is sufficiently larger than a cell and that is geometric, such as a straight or curved line of the edge of the culture container 2. Therefore, by recognizing a linear pattern extending substantially in the same direction in the image enlarged to an extent that the cells are observable, it can be determined whether or not there is an edge of the culture container 2 within the image. The usability determining unit 7 determines that the image is usable if there is no edge of the culture container 2 appearing in the image.

If the exterior of the culture container 2 appears in the image, there would be an extremely small number of structural objects as compared with the image in which the cells within the culture container 2 appear. Therefore, it can be determined whether or not the exterior of the culture container 2 appears in the image based on a variance of brightness values within the image. The usability determining unit 7 determines that the image is usable if the exterior of the culture container 2 does not appear in the image.

The determination of whether or not the image is identical to an already-acquired image can be performed by comparing the number of cells in a preceding image stored in the storage unit 9 with the number of cells in the newly-acquired image and determining that the photographed image is of the same region if the rate of change in the number of cells is lower than or equal to a predetermined threshold value. The usability determining unit 7 determines that the image is usable if the image is not identical to the already-acquired image.

When the usability determining unit 7 determines that the image is usable, the number-of-cells counting unit 8 recognizes the cells within the image and counts the number of cells. The cells can be recognized by employing a freely-chosen method, such as shape recognition. The storage unit 9 integrates and stores the number of cells counted by the number-of-cells counting unit 8.

The number-of-cells calculating unit 10 averages out integrated values, with respect to a predetermined number N of images, of the number of cells counted by the number-of-cells counting unit 8 and stored in the storage unit 9 and multiplies the calculated average value by a ratio of the effective surface area of the culture surface 2a of the culture container 2 to the surface area of the field-of-view range, thereby calculating the number of cells in the entire culture container 2.

A cell analysis method using the cell analysis device 1 according to this embodiment having the above-described configuration will be described below.

Figure 2:
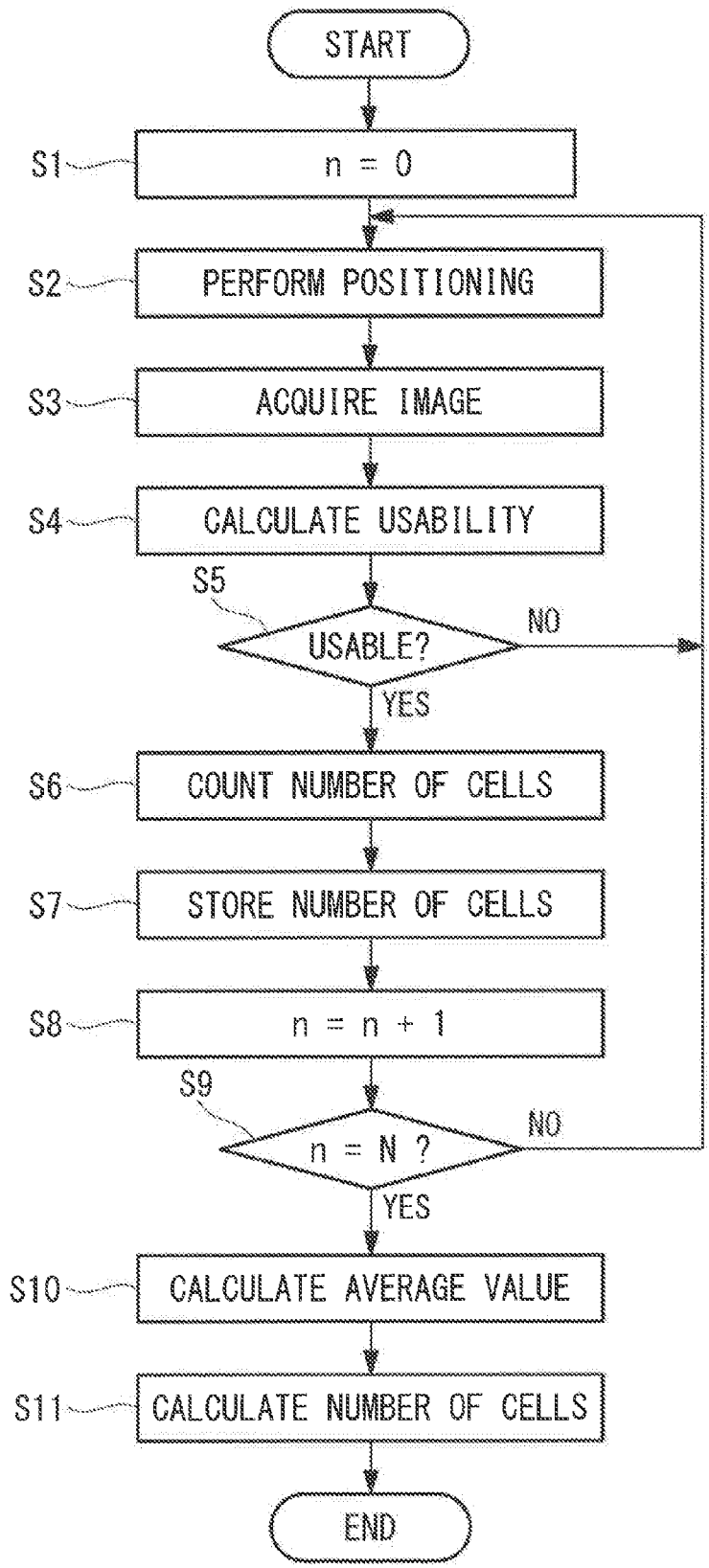
FIG. 2 is a flowchart illustrating a cell analysis method, according to an embodiment of the present invention, using the cell analysis device in FIG. 1.

First, as shown in FIG. 2, in order to calculate the number of cells within the culture container 2 by using the cell analysis method according to this embodiment, the number n of images is reset (step S1). Then, the objective lens 5 of the cell-image acquiring unit 3 is set to face the culture surface 2a of the culture container 2 in which cells are cultured, and the optical axis of the objective lens 5 is positioned at an appropriate position (step S2). The light detector 6 then detects light returning from the culture container 2 and collected by the objective lens 5, so that an image is acquired (photographing step S3).

As a result of the photographing step S3, a clipped phase-contrast image of cells in a partial range within the culture container 2 is acquired.

Subsequently, a usability calculation process with respect to at least one of the aforementioned four criteria is performed based on a brightness value of the image acquired in the photographing step S3 (step S4), and a usability determination process is performed (usability determining step S5).

In step S4, image processing for determining whether or not the image is usable is performed, and information indicating whether the image is usable or unusable is output.

If it is determined in the usability determining step S5 that the image is unusable, at least one of the culture container 2 and the objective lens 5 is moved relatively in a direction orthogonal to the optical axis of the objective lens 5, and the process from step S2 and onward is repeated.

If it is determined in the usability determining step S5 that the image is usable, the number of cells in the image is counted (number-of-cells counting step S6). Then, the counted number of cells is added to the number of cells previously stored in the storage unit 9 and is stored as an integrated value into the storage unit 9 (step S7), and the number of images n is incremented (step S8).

Subsequently, it is determined whether or not the number of cells has been counted for a predetermined number N of images (step S9). If not counted, the process from step S2 and onward is repeated.

If the number of cells has been counted for the predetermined number N of images, the number-of-cells calculating unit 10 divides the integrated value of the number of cells within a field-of-view range counted for the predetermined number N of images stored in the storage unit 9 by the predetermined number N of images, so that an average value is calculated (average-value calculating step S10).

Subsequently, the number-of-cells calculating unit 10 multiplies the average value of the number of cells calculated in the average-value calculating step S10 by the ratio of the effective surface area of the culture surface 2a of the culture container 2 to the surface area of the field-of-view range, so that the number of cells in the entire culture container 2 is calculated (number-of-cells calculating step S11).

The field-of-view range according to the image acquired by the cell-image acquiring unit 3 is set in advance, and the effective culture surface area in which cells are substantially cultured on the culture surface 2a of the culture container 2 is also set in advance. Thus, by multiplying the ratio of the effective culture surface area to the surface area of the field-of-view range by the number of cells counted by the number-of-cells counting unit 8, the number of cells within the entire culture container 2 can be calculated readily and accurately.

Accordingly, in the cell analysis device 1 and the cell analysis method according to this embodiment, the image processing unit 4 determines the usability indicating whether or not the acquired image is suitable for counting the number of cells before the number of cells is actually counted. If the image is determined to be unusable, the image is excluded from a subject to be used for counting the number of cells. This is advantageous in that the accuracy of the number of cells to be counted can be improved.

The number of cells within the culture container 2 during a culturing process can be estimated based on the number of cells counted accurately in this manner, and the cells do not need to be separated from the culture container 2. This is advantageous in that the stress on the cells being cultured can be reduced and in that the cells can grow efficiently.

Figure 3:
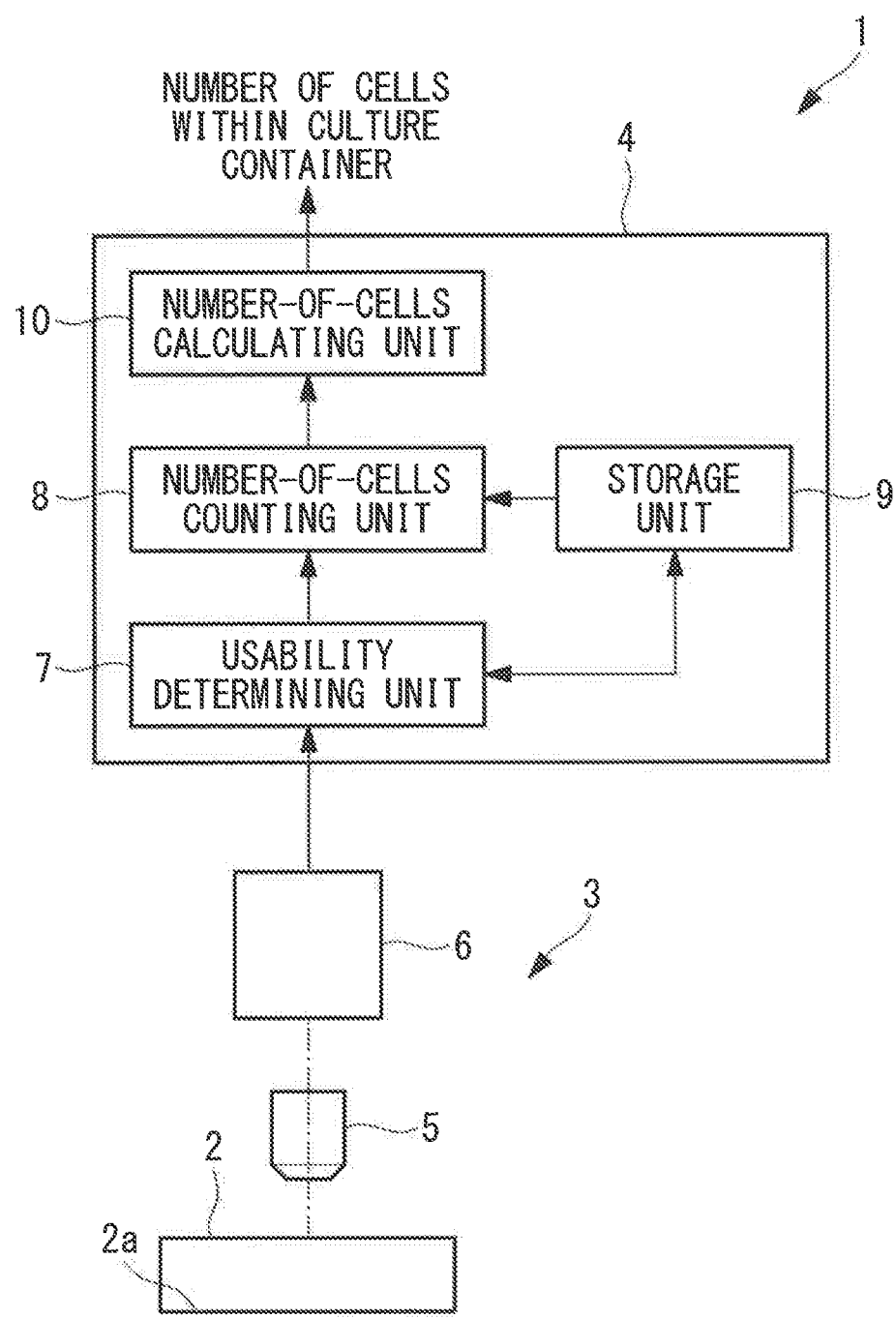
FIG. 3 illustrates the overall configuration of a modification of the cell analysis device in FIG. 1.
Figure 4:
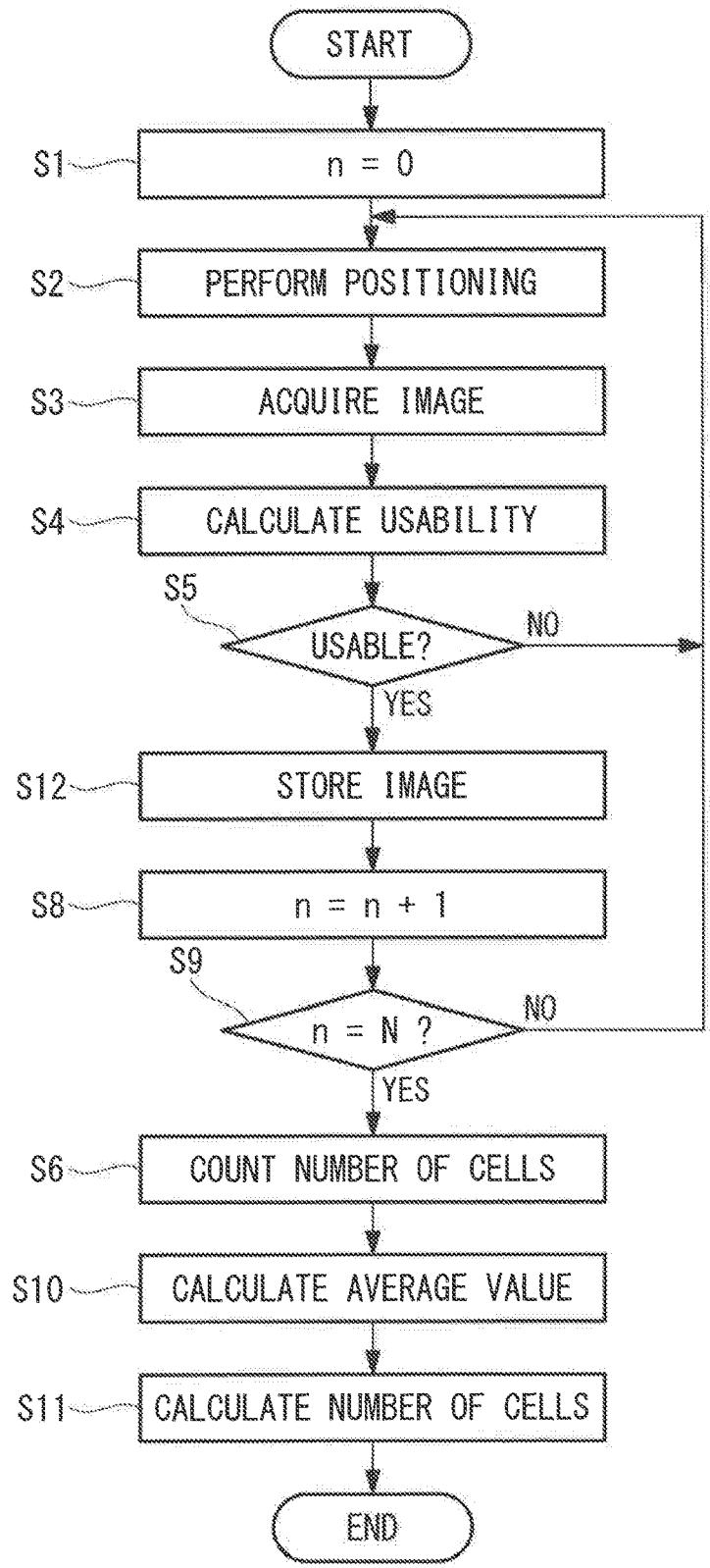
FIG. 4 is a flowchart illustrating a modification of the cell analysis method using the cell analysis device in FIG. 3.

In this embodiment, the number of cells is counted every time an image is determined to be usable by the usability determining unit 7. Alternatively, as shown in FIGS. 3 and 4, in a case where it is determined that an acquired image is usable, the image may be stored in the storage unit 9 (step S12), the number of cells may be collectively counted (number-of-cells counting step S6) after a predetermined number N of images are acquired, and an average value may be calculated (average-value calculating step S10).

As an alternative to the above-described case where an integrated value of the counted number of cells is stored in the storage unit 9, the counted number of cells may be stored separately, and the integration and division processes may be performed when calculating the average value.

Figure 5:
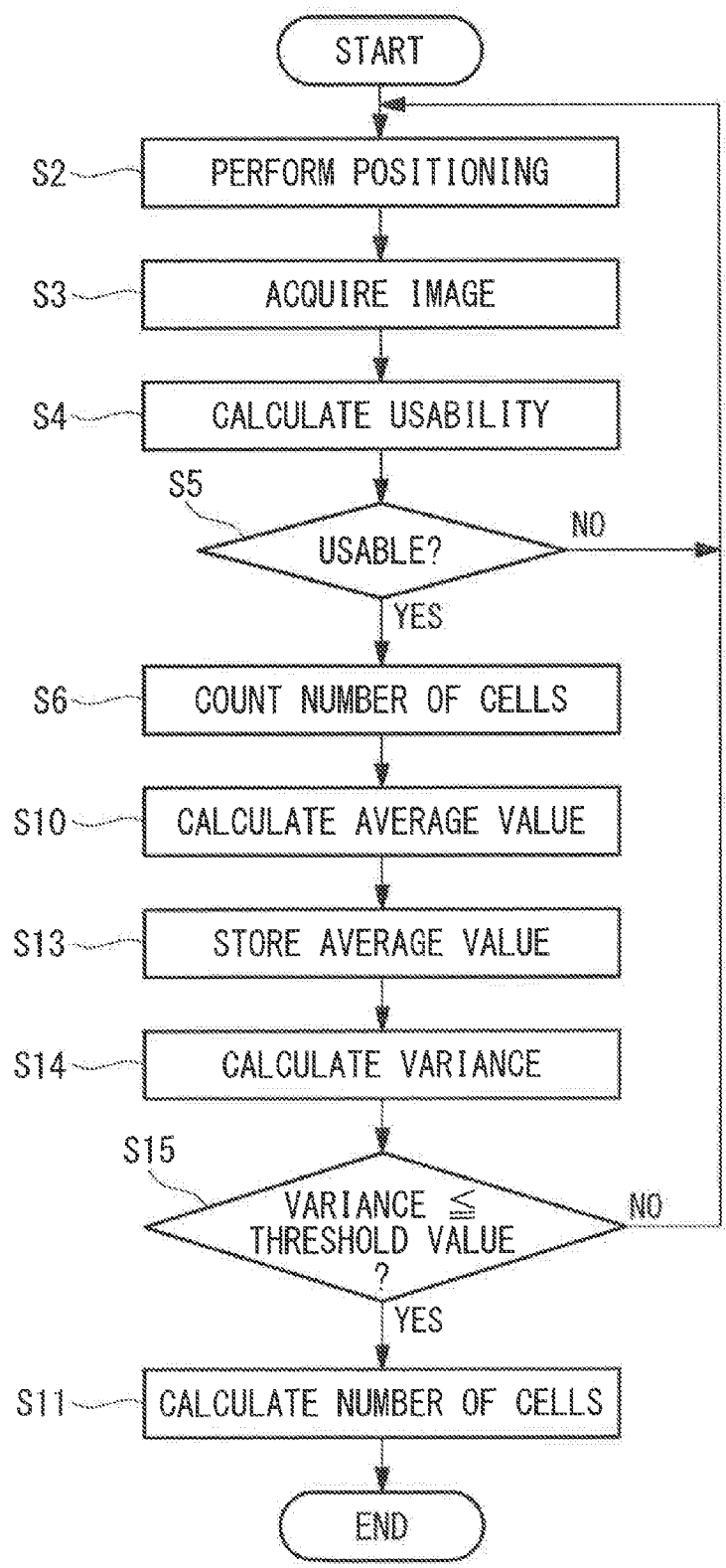
FIG. 5 is a flowchart illustrating another modification of the cell analysis method in FIG. 2.

As an alternative to this embodiment in which the number of cells is calculated upon completion of image acquisition when it is determined that a predetermined number N of images are usable, an average value of the number of cells may be calculated (step S10) and stored (step S13), and a variance thereof may be calculated (step S14), without counting the number n of images, as shown in FIG. 5. Then, when a condition that the variance of the average value of the number of cells becomes smaller than or equal to a predetermined threshold value is satisfied (step S15), the image acquisition may be terminated and the number of cells may be calculated (step S11). If the variance of the average value of the number of cells is larger than the predetermined threshold value, the process from step S2 and onward is repeated without calculating the number of cells.

With the variance of the average value of the number of cells, it can be more reliably determined that the interior of the culture container 2 has been sufficiently sampled.

In this embodiment, the number of colonies may be counted as the number of cells.

As a result, the following aspect is read from the above described embodiment of the present invention.

An aspect of the present invention provides a cell analysis device including a cell-image acquiring unit that acquires an image of cells within a culture container in which the cells are cultured, a usability determining unit that determines whether or not the image acquired by the cell-image acquiring unit is usable, a number-of-cells counting unit that counts the number of cells within the image determined as being usable by the usability determining unit, and a number-of-cells calculating unit that calculates the number of cells within the culture container based on the number of cells counted by the number-of-cells counting unit.

According to this aspect, the usability determining unit determines whether or not the image within the culture container acquired as a result of the operation of the cell-image acquiring unit is usable, and the number-of-cells counting unit counts the number of cells within the image determined that it is usable. Thus, an image in which cells do not appear in a state suitable for counting the number of cells is excluded from a subject to be used for counting the number of cells. Ultimately, the number of cells within the culture container to be calculated by the number-of-cells calculating unit can be calculated accurately.

In the above aspect, the usability determining unit may detect blurriness in the image and may determine that the image is usable if the image has no blurriness.

Accordingly, if there is blurriness in an image, the image is excluded from a subject to be used for counting the number of cells, whereby the number of cells can be accurately calculated based on an image with no blurriness.

In the above aspect, the usability determining unit may detect whether or not an edge of the culture container appears in the image and may determine that the image is usable if the edge of the culture container does not appear in the image.

Accordingly, if an edge of the culture container appears in the image, the image is excluded from a subject to be used for counting the number of cells, whereby the number of cells can be accurately calculated based on an image in which an edge does not appear.

In the above aspect, the usability determining unit may detect whether or not an exterior of the culture container appears in the image and may determine that the image is usable if the exterior of the culture container does not appear in the image.

Accordingly, if an exterior of the culture container appears in the image, the image is excluded from a subject to be used for counting the number of cells, whereby the number of cells can be accurately calculated based on an image in which an exterior of the container does not appear.

In the above aspect, the number-of-cells calculating unit may calculate the number of cells by using an average value of the number of cells counted from a plurality of images, and the usability determining unit may detect whether or not the image is identical to an already-acquired image and may determine that the image is usable if the image is not identical to the already-acquired image.

Accordingly, the number of cells within the culture container is calculated by the number-of-cells calculating unit on the basis of the average value of the number of cells within the plurality of images counted by the number-of-cells counting unit. In this case, an improvement in the accuracy by averaging cannot be expected if an image identical to an already-acquired image is used. Therefore, by excluding such an image, the number of cells can be calculated accurately.

Another aspect of the present invention provides a cell analysis method including a photographing step of acquiring an image of cells within a culture container in which the cells are cultured, a usability determining step of determining whether or not the image acquired in the photographing step is usable, a number-of-cells counting step of counting the number of cells within the image determined as being usable in the usability determining step, and a number-of-cells calculating step of calculating the number of cells within the culture container based on the number of cells counted in the number-of-cells counting step.

In the above aspect, the usability determining step may include detecting blurriness in the image and determining that the image is usable if the image has no blurriness.

In the above aspect, the usability determining step may include detecting whether or not an edge of the culture container appears in the image and determining that the image is usable if the edge of the culture container does not appear in the image.

In the above aspect, the usability determining step may include detecting whether or not an exterior of the culture container appears in the image and determining that the image is usable if the exterior of the culture container does not appear in the image.

In the above aspect, the number-of-cells calculating step may include calculating the number of cells by using an average value of the number of cells counted from a plurality of images, and the usability determining step may include detecting whether or not the image is identical to an already-acquired image and determining that the image is usable if the image is not identical to the already-acquired image.

REFERENCE SIGNS LIST 1 cell analysis device
2 culture container
3 cell-image acquiring unit
7 usability determining unit
8 number-of-cells counting unit
10 number-of-cells calculating unit
S3 photographing step
S5 usability determining step
S6 number-of-cells counting step
S11 number-of-cells calculating step

The invention claimed is:

1. A cell analysis device comprising:
an image sensor;
a lens; and
a processor comprising hardware, the processor configured to:
acquire an image of cells with the image sensor, through the lens, within a culture container in which the cells are cultured;
determine whether or not the image acquired is usable as an image for counting a number of cells, wherein the processor detects whether or not an edge of the culture container appears in the image and determines that the image is usable if the edge of the culture container does not appear in the image;
count the number of cells within the image determined as being usable; and
calculate the number of cells within the culture container based on the number of cells counted.

2. The cell analysis device according to claim 1, wherein the processor is further configured to detect blurriness in the image and determines that the image is usable if the image has no blurriness.

3. The cell analysis device according to claim 1, wherein the processor is further configured to detect whether or not an exterior of the culture container appears in the image and determines that the image is usable if the exterior of the culture container does not appear in the image.

4. The cell analysis device according to claim 1, wherein the processor is further configured to calculate the number of cells by using an average value of the number of cells counted from a plurality of images, and
wherein the processor is further configured to detect whether or not the image is identical to an already-acquired image and determines that the image is usable if the image is not identical to the already-acquired image.

5. A cell analysis method comprising:
acquiring an image of cells with an image sensor, through a lens, within a culture container in which the cells are cultured;
determining whether or not the acquired image is usable as an image for counting a number of cells, wherein detecting whether or not an edge of the culture container appears in the image and determining that the image is usable if the edge of the culture container does not appear in the image;
counting the number of cells within the image determined as being usable; and
calculating the number of cells within the culture container based on the counted number of cells.

6. The cell analysis method according to claim 5, wherein detecting blurriness in the image and determining that the image is usable if the image has no blurriness.

7. The cell analysis method according to claim 5, wherein detecting whether or not an exterior of the culture container appears in the image and determining that the image is usable if the exterior of the culture container does not appear in the image.

8. The cell analysis method according to claim 5, wherein calculating the number of cells by using an average value of the number of cells counted from a plurality of images, and
wherein detecting whether or not the image is identical to an already-acquired image and determining that the image is usable if the image is not identical to the already-acquired image.

* * * * *